United States Patent [19]

Zucker et al.

[11] 4,447,535

[45] May 8, 1984

[54] PROCESS FOR THE RECOVERY OF A CONCENTRATED STILLAGE

[75] Inventors: Friedrich J. Zucker; Georg Osthaus, both of Neuss, Fed. Rep. of Germany

[73] Assignee: Supraton F. J. Zucker GmbH, Neuss, Fed. Rep. of Germany

[21] Appl. No.: 484,929

[22] Filed: Apr. 14, 1983

Related U.S. Application Data

[63] Continuation of Ser. No. 275,447, Jun. 22, 1981, abandoned.

[30] Foreign Application Priority Data

Jun. 26, 1980 [DE] Fed. Rep. of Germany ....... 3023874

[51] Int. Cl.$^3$ .............................................. C12P 7/14
[52] U.S. Cl. .................................. 435/162; 435/161; 435/96; 435/99
[58] Field of Search ................. 435/161, 162, 165, 96, 435/99, 813

[56] References Cited

U.S. PATENT DOCUMENTS

| 385,625 | 7/1888 | Horne | 435/165 |
| 504,074 | 8/1893 | Bradley et al. | 435/165 |
| 3,337,414 | 8/1967 | Wilson | 435/95 |
| 3,897,305 | 7/1975 | Hurst | 435/96 |
| 3,910,820 | 10/1975 | Holt et al. | 435/96 |
| 3,912,590 | 10/1975 | Slott et al. | 435/99 |
| 3,922,197 | 4/1975 | Leach et al. | 435/96 |
| 4,376,163 | 3/1983 | Ehnstrom | 435/165 X |

FOREIGN PATENT DOCUMENTS 1922932 11/1970 Fed. Rep. of Germany.

*Primary Examiner*—R. B. Penland
*Attorney, Agent, or Firm*—Merriam, Marshall & Bicknell

[57] ABSTRACT

A concentrated stillage with a high solids content may be recovered in such a manner that starch or starch-containing raw materials in a suitably crushed form are coaxially introduced into the center of a homogenizer together with enzymes, which are suitable for making alcohol, while simultaneously introducing steam and are suddenly gelatinized therein mechanically and thermally at temperatures of not less than 50° C. and not more than 115° C. while ultrafinely dividing the enzyme; the starch paste after liquefaction is converted to the glucose and the resultant mash is fermented in such a manner that the stillage obtained with reduced dry matter, after removal of merely the coarse contaminations by, for example, centrifuging is repeatedly recycled without further purification and reused as process liquor.

2 Claims, No Drawings

{ 4,447,535 }

PROCESS FOR THE RECOVERY OF A CONCENTRATED STILLAGE

This is a continuation of application Ser. No. 275,447, filed June 22, 1981, now abandoned.

This invention relates to a process for the recovery of a concentrated stillage in the process of producing alcohol from starch or starch-containing raw materials.

BACKGROUND OF THE INVENTION

A known problem of ethanolic fermentation are the low substrate concentrations in the fermentation process, which permits the recovery of a stillage which has a content of dry substance of only about up to 8% when operating in the previously usual manner. As is known, this dry matter contains as essential constituents above all amino acids, proteins and salts in addition to residual sugar and, in view of this fact, the stillages, above all the potato and cereal stillages, have a high feed value which doubtlessly would be still higher if the proportion of solids in the stillage could be increased. Theoretically, this would have to be accomplished by repeated recycling of the stillage during the alcoholic fermentation, and repeated recycling would have to permit a corresponding increase by several times. However, it has been found in practice that repeated recycling of the stillage is not possible since the thermal digestion of the starch or the starch-containing raw materials results in the formation of by-products which impair the subsequent fermentation by means of yeasts. These by-products include, for example, the products of the Maillard reaction between proteins and carbohydrates.

As is known, starch is a carbohydrate which is not directly fermentable so it must initially be converted by means of enzymes to form fermentable sugars before the alcoholic fermentation is possible. It is initially necessary to this end to digest the starch-containing raw materials, which detaches the starch cells from their cell associations and opens them and releases the starch which can then be gelatinized and saccharified more readily. In the so-called steaming process, this digestion is effected in most cases in the HENZE steamer at elevated temperatures under pressure and is followed by expansion and cooling and subsequent addition of enzyme to saccharify the digested and gelatinized starch. This is a discontinuous process which is to be carried out batchwise and in which the starch raw material needs about 1.5 to 2 hours at a temperature up to 150° C. for its gelatinization. Apart from the HENZE steamer, use is partially made also of jet digesters, but the temperature in these digesters is also relatively high and generally ranges between 105° C. and 115° C.

A process for the gelatinization of starch or starch-containing products with substantial saving of energy is also described in German Pat. No. 19 22 932. In this process, steam and starch suspension are introduced coaxially into the center of a homogenizer and the gelatinization of the starch is effected in a zone of high density of shear and cavitation forces. In this known process, there can be used successfully a homogenizer which consists of a housing and a truncated conical rotor, which rotates in the housing and has a surface having coaxial rings of increasing diameter which extend to or mesh with recesses between similar rings on the housing interior wall lying opposite the rotor. This process also still uses comparatively high temperatures even though these are lower than the temperatures usual in the HENZE steamer and in the jet digester.

THE INVENTION

It is an object of the invention to provide a process which makes it possible in the production of alcohol from starch or starch-containing raw materials to reduce the amount of the products inhibiting the fermentation such as the Maillard compounds to an extent such that a concentrated stillage can be recovered by the fact that it can be recycled repeatedly, which permits an increase in its content of solids.

This object is accomplished by a process for the recovery of a concentrated stillage in the production of alcohol from starch or starch-containing raw materials, said process being characterized in that starch or starch-containing raw materials in a suitably crushed form are coaxially introduced into the center of a homogenizer together with enzymes which are suitable for making alcohol while simultaneously introducing steam and are suddenly gelatinized therein mechanically and thermally at temperatures of not less than 50° C. and not more than 115° C. while ultrafinely dividing the enzyme; the starch paste after liquefaction is converted to the glucose and the resultant mash is fermented in such a manner that the stillage obtained with reduced dry matter, after removal of merely the coarse contaminations by, for example, centrifuging is repeatedly recycled without further purification and reused as process liquor until the proportion of solids in the stillage has increased to about 30% dry substance. Preferably the gelatinization is effected at temperatures between 85° C. and 95° C.

In this process, the starch-containing roots of the manihot bush may also be used as raw materials in addition to potatoes, cereals, especially rye, wheat, maize, rice or millet.

An apparatus of the type described above may be preferably used in this process as the homogenizer which, for example, is described also in U.S. Pat. No. 3,995,838 and consists of a housing and a truncated conical rotor which rotates in the housing and has a generated surface which is equipped with coaxial rings of stepped diameters which are staggered with similar rings on the interior wall of the housing lying opposite the rotor.

The particular advantage of the process according to the invention consists in the fact that the gelatinization of the starch-containing raw materials is effected at temperatures of only about 70° C. to 90° C. and that only very low amounts of products of the Maillard reaction are formed at these comparatively low temperatures.

A further substantial advantage of the process according to the invention consists in the fact that it can be carried out at starch concentrations of up to 40% dry substance. It is possible in this manner when using fresh bulbs or roots which generally contain about 40% of dry substance to use at least part of the stillage as diluting water. If the kinds of cereals mentioned above are used as starch-containing raw materials, the stillage is used as what is known as water of partial solution.

According to the invention, the stillage may be recycled repeatedly, i.e. about three to four times, and reused as process liquor. Since the proportion of solids increases to about 30% of dry substance when operating in this manner, an amount of liquid which is by far lower than that previously necessary needs be evaporated when subsequently using the concentrated stillage as feeding-stuff. Additionally, the quantity of stillage as such is reduced to about one fourth of the amount previously obtained conventionally thereby solving also simultaneously additional waste water problems. However, a particular advantage of the process according to the invention consists in the fact that, due to the repeated recycling of the stillage, it is not necessary to drive the fermentation down as far as heretofore because the residual sugar contained in the stillage is repeatedly returned into the fermentation batch where it is also fermented.

The invention is further illustrated by the example which follows.

EXAMPLE

A starting mixture (containing about 35% of dry substance) is prepared from 40 kgs of grain (containing about 12% of water) or tapioca flour (containing about 12% of water) and introduced coaxially into the center of a homogenizer while simultaneously introducing steam. After gelatinization at about 70° C., the starch is liquefied enzymatically, thereafter diluted 1:1 with water and saccharified enzymatically (resulting in about 200 liters of sweet mash containing approximately 17% of dry substance) which is thereafter fermented in a manner known per se.

The stillage obtained when distilling the fermentation product contains about 11% of dry substance. It is freed from contaminating coarse matter such as yeast cells by centrifuging, which results in about 190 kgs of stillage containing about 9% of dry substance. An amount of 160 kgs of this stillage containing 9% of dry substance is again mixed with 40 kgs of raw material and, in the manner described above, gelatinized and fermented and, after distillation, freed from coarse matter by centrifuging. This results again in the recovery of about 190 kgs of stillage which now contains 17% of dry substance. Thus, when mixing with the remaining 30 kgs of stillage having 9% of dry substance from the previous batch, a total of 220 kgs of stillage containing about 16% of dry substance is obtained. In this manner, it is possible already with one recycle of stillage to reduce the fresh water necessary for carrying out the process by 100%, the total amount of stillage produced by 27% and the cost necessary for evaporating by 45%.

Altogether, it is possible in accordance with the invention to recycle the process liquor at least three to four times.

It is also possible, of course, to use only part of the stillage as diluting and cooling water of the concentrated mash, but this diminishes the advantages mentioned above.

What is claimed is:

1. A process for the recovery of a concentrated stillage in the production of alcohol from starch or starch-containing raw materials, comprising the steps of:
   (a) mixing said starch or starch-containing materials in finely divided form with an aqueous process liquor;
   (b) introducing the mixture from step (a) together with steam and enzymes suitable for making alcohol coaxially to the center of a rotor-stator homogenizer wherein the starch is rapidly gelatinized thermally and mechanically in a zone of high density of shear and cavitation forces at a temperature between 70° C. and 115° C. and the enzyme is ultrafinely distributed;
   (c) enzymatically liquefying the starch in the product of step (a);
   (d) saccharifying and fermenting the product of step (c);
   (e) distilling the product of step (d) to produce alcohol and stillage;
   (f) separating solid coarse particles from said stillage; and
   (g) repeating the cycle of steps (a) through (f) using the stillage essentially as obtained from step (f) at least three times without further purification as the process liquor in step (a), until the dry solids content of the stillage has increased to about 30%.

2. A process according to claim 1 wherein the gelatinization is effected at temperatures between 85° C. and 95° C.

* * * * *